United States Patent [19]

Faust et al.

[11] 4,346,113

[45] Aug. 24, 1982

[54] PROCESS FOR THE CONTINUOUS FERMENTATION OF AQUEOUS SLURRIES FOR THE PRODUCTION OF ALCOHOL AND YEAST BIOMASS

[75] Inventors: Uwe Faust, Fischbach; Paul Präve, Neuenhain; Beate Dorsemagen, Frankfurt; Norbert Hofer, Eppstein, all of Fed. Rep. of Germany

[73] Assignee: UHDE GmbH, Dortmund, Fed. Rep. of Germany

[21] Appl. No.: 188,345

[22] Filed: Sep. 18, 1980

[30] Foreign Application Priority Data

Sep. 21, 1979 [DE] Fed. Rep. of Germany ....... 2938339

[51] Int. Cl.³ .......................... C12P 7/06; C12G 3/02
[52] U.S. Cl. ....................................... 426/12; 426/14; 426/60; 435/161; 435/256; 435/804
[58] Field of Search ...................... 426/60, 11, 12, 14; 435/161, 256, 804

[56] References Cited

U.S. PATENT DOCUMENTS

| 2,676,137 | 4/1954 | Schneider | 435/161 |
|---|---|---|---|
| 3,120,473 | 2/1964 | Deloffre | 426/60 |
| 3,384,553 | 5/1968 | Caslavsky et al. | 426/60 |
| 3,563,759 | 2/1971 | Wolter et al. | 426/11 |
| 3,868,305 | 2/1975 | Masuda et al. | 426/60 |
| 4,064,015 | 12/1977 | Nyiri et al. | 435/161 |
| 4,080,260 | 3/1978 | Chao | 426/60 |

*Primary Examiner*—Jeanette M. Hunter
*Attorney, Agent, or Firm*—Wilson, Fraser, Barker & Clemens

[57] ABSTRACT

A continuous process for the production of alcohol and yeast biomass by reaction in a uniform fermenting mixture of a sugar-bearing, aqueous slurry, starter yeast, yeast nutrients and an oxygen-bearing gas, wherein the yeast is a flocculating, bottom yeast, the portion of the wort which remains after separation of the alcohol-bearing medium therefrom, is recycled to the fermenting mixture, the oxygen-bearing gas is dispersed homogeneously throughout the fermenting mixture, and is introduced to maintain a mean-free oxygen concentration not greater than 1 ppm in the aqueous phase, and the process is controlled to maintain the measurable free sugar concentration in the fermenting mixture at a level which does not exceed 0.1 percent by weight, and to maintain the active yeast concentration in the fermenting mixture between 100 and 110 percent of the specific degree of fermentation.

4 Claims, 1 Drawing Figure

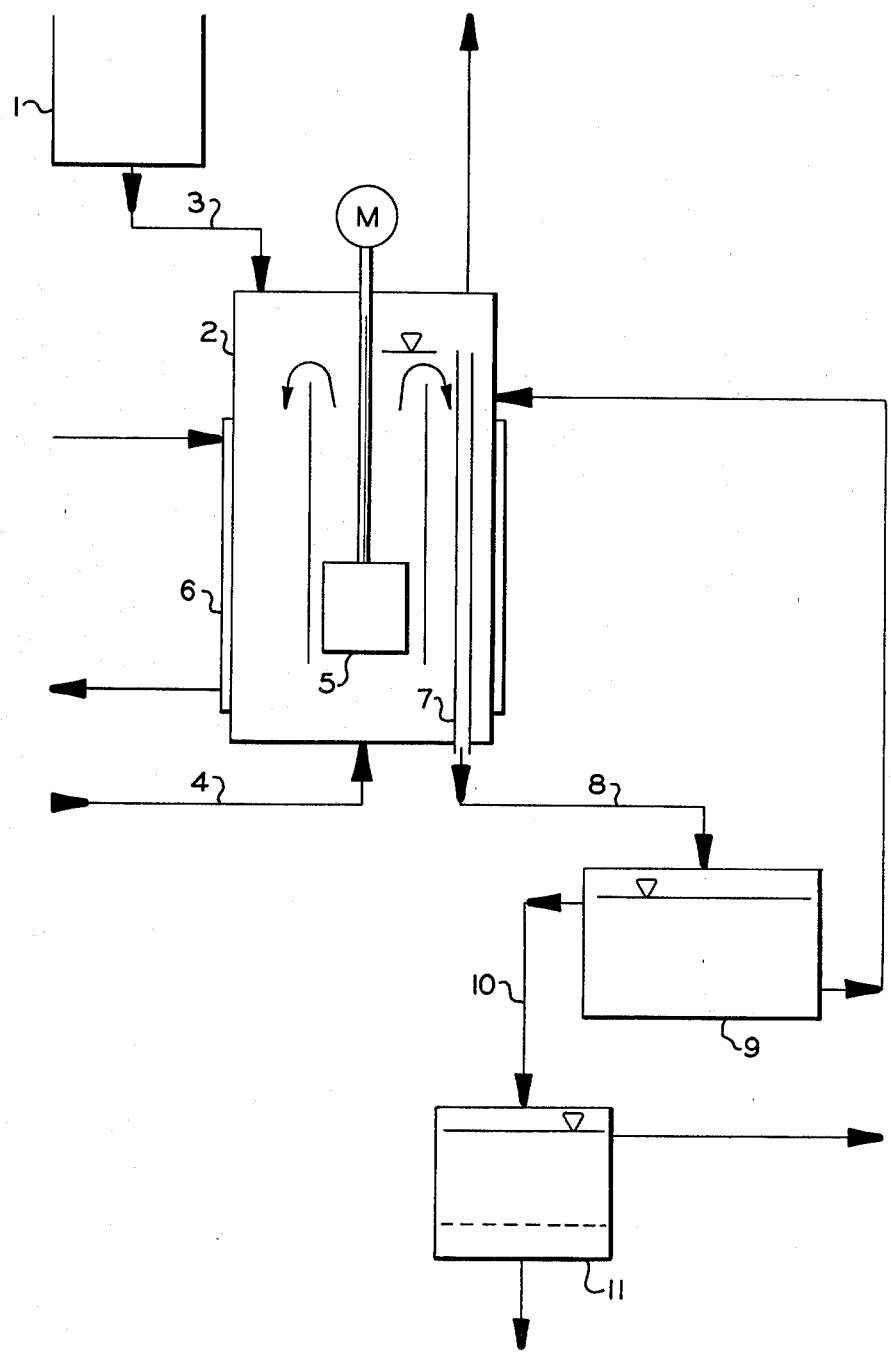

PROCESS FOR THE CONTINUOUS FERMENTATION OF AQUEOUS SLURRIES FOR THE PRODUCTION OF ALCOHOL AND YEAST BIOMASS

BACKGROUND OF THE INVENTION

The continuous production of ethyl alcohol has aroused considerable interest in recent years because it allows a further source of energy to be exploited and because it offers large-scale industrial units the advantages of uniform production, simpler control and a possible increase in productivity by avoiding cleaning and start-up phases. For the continuous fermentation of alcohol it is necessary that an adequate supply of sugar-bearing substrate, the so-called slurry be available to the microorganisms and that the extremely favourable fermentation conditions be maintained.

Traditionally, the commercial-scale production of ethyl alcohol by means of fermentation with yeasts has hitherto been using batch processes, i.e. the sugar-bearing substrate to be converted was placed in an aqueous solution in a fermenter, inoculated with starter yeast and left to ferment. During this period, the yeast microorganisms convert the sugar contained in the substrate to ethyl alcohol and carbon dioxide according to the following formula:

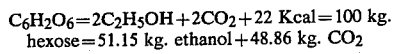
$$C_6H_2O_6 = 2C_2H_5OH + 2CO_2 + 22 \text{ Kcal} = 100 \text{ kg.}$$
$$\text{hexose} = 51.15 \text{ kg. ethanol} + 48.86 \text{ kg. } CO_2$$

The process is anaerobic and therefore the system does not require an air supply. When all of the sugar has been converted, the contents of the fermenter are harvested and subjected to distillation, during which the desired ethanol is obtained. Technical improvements, such as controlled addition of the starter yeast, maintaining the temperature at a constant level by cooling, controlling the pH, adding microbiological nutrients as well as mechanical mixing of the fermentation system resulted in an increase in yield and improved the conversion rate.

Because only small industrial units can be used for batch operation and uniform production cannot be achieved, there has been an increasing trend towards the continuous fermentation of aqueous slurries, and various processes have been developed for this purpose. It became more and more common to use processes in which the fermentation steps were separated with regard to space and time, in other words, the effect of the catalyst on the yeast on the one hand and the maintenance of the anaerobic yeast metabolism, i.e. yeast growth and reproduction on the other hand. This inevitably resulted in multi-stage processes. In the first stages the yeast cells reproduce with an oxygen surplus. The subsequent stages center around the anaerobic conversion of sugar to alcohol. A final stage aims at quantitatively converting all the residual substrate and obtaining a maximum alcohol concentration. It is unavoidable with such a process that one or other of the permissible limit parameters is exceeded or may not be met, thus damaging the biocatalyst and/or impairing the reaction.

In DE-AS No. 23 54 556 a continuous process is suggested in which alcohol and yeast biomass are produced alternately. In this process, the amount of slurry fed to the fermenter is controlled in such a way as to produce a concentration of fermentable substrate of max. 5 g/l in terms of glucose. If mainly alcohol is to be produced, the oxygen will be admixed in controlled quantities in such a way that 1 g. of yeast in the fermenter can consume 0.2-5 mg. oxygen/hour and when yeast biomass is produced the oxygen is fed at a rate of max. 400 mg/g yeast dry substance produced. This process exhibits a broad range of oxygen feed rates, i.e. up to a factor of 25, in fermentation and a high oxygen feed rate in yeast production. It is not guaranteed that the optimum oxygen concentration for fermentation is present in all process stages.

SUMMARY OF THE INVENTION

The processes known up to now are based on the idea that the production of yeast biomass and the fermentation to alcohol must proceed as two separate reactions at different times.

It was surprising to find that, according to the invention, the process for the continuous fermentation of aqueous slurry for the production of alcohol and yeast biomass in a fermenter and in a pertaining separation stage, with aqueous slurry, starter yeast, a nutrients mixture and oxygen-bearing gas being fed to the fermenter, can be performed in such a manner that the concentration of the slurry introduced, referred to the sugar content, corresponds to the attainable degree of conversion to yeast and alcohol, with the result that:

the measurable free sugar concentration in the fermenter does not exceed 0.1% by weight, a homogeneous, defined mixture is adjusted in the fermenter by known means, the active yeast concentration within the reaction space is maintained between 100% and 110% of the specific degree of fermentation by recycling alcohol- and yeast-bearing medium from the separation stage, oxygen-bearing gas is dispersed homogeneously and fed at a uniform rate, and a mean free oxygen concentration of 1 ppm in the liquid phase is not exceeded, a flocculating bottom yeast is used, and that de-yeasted, alcohol bearing medium is separated from the yeast- and alcohol-bearing medium contained in the cycle and is removed from the separation stage.

According to another embodiment of the invention, the oxygen-bearing gas may be air.

An advantageous development is produced when the residence period of the yeast- and alcohol-bearing medium in the separation stage is not more than 30 minutes, preferably 5-15 minutes.

It is an essential feature of the invention that, according to the new teaching, the process for the continuous fermentation of slurry is operated in such a way that yeast biomass is regenerated both intentionally and in a controlled manner. It was found that, with the correct setting of the limit parameters in the fermenter, the production of fully-active, self-reproducing yeast cells and the fermentation proceed quasi-simultaneously. Contrary to the opinion of the experts, the very low oxygen surplus of max. 1 ppm has no adverse effect at all on the fermentation process. The yeast cells consume the oxygen in such a preferable way for their growth and reproduction that the simultaneous fermentation is not disturbed. In view of the fact that anaerobic conditions also prevail within the cells because of the limited oxygen supply, but at the same time an adequate supply of slurry is available, the fermentation of the slurry takes place simultaneously.

Optimum production is achieved due to the controlled admission of sugar-bearing raw materials, oxygen and fresh yeast and the exact maintenance of the limit parameters, with the reactions proceeding simultaneously. By controlling the yeast production, an intentional limiting of the oxygen is attained and, consequently, specific production of alcohol by the yeast cells. The alcohol content in the cycle, which is low compared with other known processes, has no adverse effect on the yeast cells. The slurry, which is depleted of sugar, rich in alcohol and mixed with yeast, is withdrawn from the fermenter and fed to the separation stage.

BRIEF DESCRIPTION OF THE DRAWING

FIG. 1 is a flow diagram of the process.

DETAILED DESCRIPTION OF THE PREFERRED EMBODIMENTS

The process is described in the following examples and in the flow diagram, which represents a preferred configuration.

EXAMPLE 1

A beet molasses/nutrient solution slurry with the following composition is prepared in the nutrient solution receiver 1, which has a capacity of approx. 300 l:

| quantities per 1: | 250 | g. beet molasses |
|---|---|---|
| | 2 | g. $(NH_4)_2 SO_4$ |
| | 0.32 | g. $KH_2, PO_4$ |
| | 0.5 | g. $CaCl_2$ |
| | 0.12 | g. $Mg SO_4$ |
| | 800 | ml. tap water |

The pH value is adjusted to 4 by the addition of $H_2SO_4$. *Sacharomyces uvarum* is used as a microorganism. After a growth phase of the yeast in the fermenter 2 (capacity 1 l), slurry from the nutrient solution receiver 1 is fed continuously to this fermenter via the line 3. The intake point for the nutrient solution is the fermenter head. At the same time, 0.05 vvm ( $\triangleq$ 3 l/h) air is fed to the fermenter via line 4. The fermenter 2 is equipped with a three-stage paddle wheel 5 with head drive, a pH meter (not illustrated), and a temperature controller 6. The fermentation temperature is set and maintained at 35° C.

After an initial fermentation period, the fermented yeast- and alcohol-bearing wort is continuously withdrawn at a rate of 4 l/h via the internal overflow pipe 7 and the line 8 into the separation vessel 9, which has a capacity of 300 ml. The separation vessel is equipped with a slowly rotating agitator. The filtrate with a low yeast content, which forms on the surface of the contents of the separation vessel is withdrawn at a rate of 1 l/h through a vertically adjustable nozzle located at the side, which simultaneously serves as a level controller, via the line 10 into the collecting vessel 11, which has a capacity of 15 l. The alcohol content of the filtrate is 6.5% by vol., which corresponds to a theoretical yield of more than 95% of the sugar used in the nutrient solution.

The suspension, the alcohol content of which is almost as high as that of the filtrate, is withdrawn from the separation vessel 9 and returned to the fermenter 2 by means of an air-lift pump at a rate of 3 l/h.

The yeast still contained in the filtrate precipitates in the amply-sized collecting vessel 11 and is removed at intervals. This yeast is the surplus yeast which is due to the yeast growth. Only yeast-free wort is withdrawn from the collecting vessel 11 for the production of alcohol.

The yeast concentration in the cycle system, i.e. in the fermenter 2 and in the separation vessel 9 is 70 g/l dry substance.

The nutrient solution receiver with a capacity of 300 l. was emptied in 12 days, the alcohol yield during this period being uniform.

EXAMPLE 2

The apparatus described in Example 1 is fed with the same beet molasses/nutrient solution slurry, but this time using a yeast strain of the *Sacharomyces cerevisiae* type. This strain is a flocculating bottom yeast, as described in the book "Die Hafen", Band 1, Verlag Hans Carl, Nurnberg 1960, Page 187.

With this strain as well, the 300 l nutrient solution receiver was able to be emptied in 12 days. On the other hand, with a uniformly good process control, a theoretical yield of over 95% of the sugar used in the nutrient solution was attained.

EXAMPLE 3

A technical-scale apparatus according to the diagram is supplied with a beet molasses/nutrient solution slurry as described in Example 1. The yeast strain is likewise the same.

The solution is fed from the nutrient solution receiver 1, this time a 6 $m^3$ agitated vessel, in non-sterile state by means of a reciprocating pump to the fermenter 2 at the fermenter head. The fermenter 2 is a 1000 l. loop-type fermenter of known design with jet aeration, overflow level control and a temperature control system 6 in the form of shell cooling.

0.05 vvm ( $\triangleq$ 3 $Nm^3/h$) air and an additional 1 vvm ( $\triangleq$ 60 $Nm^3/h$) nitrogen are used for aeration. Aeration by means of nitrogen results in homogeneous mixing and circulation in the loop-type fermenter.

After an initial fermentation period as in Example 1, the fermented yeast- and alcohol-bearing wort is continuously withdrawn at a rate of 4 $m^3/h$ via the internal overflow pipe 7 and the line 8 into the separation vessel 9, which has a capacity of 300 l and is not equipped with an agitator. The filtrate overflows into the 150-l collecting vessel 11. The alcohol content here is also 6.5% by vol., which corresponds to a theoretical yield of over 95% of the sugar used in the nutrient solution.

The suspension, the alcohol content of which is almost as high as that of the filtrate, is withdrawn from the separation vessel 9 and returned to the fermenter at the rate of 3 $m^3/h$ by means of a Mohno pump, the discharge rate of which is variable. The filtrate and the yeast still contained in it are separated from each other in the collecting vessel 11, as in Example 1.

The yeast concentration in the cycle system is maintained as in Example 1. When the following limit parameters are maintained, the process can be performed satisfactorily for a prolonged period:

| pH value | 3.5–6 |
|---|---|
| Temperature (depending on the yeast strains used, tolerance of ± 2% within a certain temperature range) | 28–36° C. |
| Free oxygen concentration in nutrient medium | 0 ppm–1 ppm |
| concentration of free, fermentable sugar | 0%–0.1% |

| | |
|---|---|
| Free product concentration (depending on yeast strain) not more than | 8.5% by vol |

Thus, a uniform alcohol production rate was attained continuously during a production period of several days without the limit parameters and the product quality being affected.

In view of the fact that the reproduction of yeast takes place in the presence of air and sugar-bearing slurry, and the fermentation of sugar and the oxygen surplus are very limited in the presence of sugar and yeast, the admixing of the reaction partners to the slurry is controlled in such a way that the concentration of free, fermentable sugar at the outlet of the fermenter is less than 0.1%, the surplus concentration of active yeast is less than 10% and the oxygen concentration in the medium is 0.05 ppm. The mixing efficiency is responsible on the one hand for a uniform mass and heat transfer and thus for maintaining the narrow concentration and temperature ranges, and on the other hand, for the fermentation efficiency, i.e. for speedy fermentation with the lowest possible oxygen surplus.

What is claimed is:

1. In a continuous process for the production of alcohol and yeast biomass by reaction in a uniform fermenting mixture of a sugar-bearing, aqueous slurry, starter yeast, yeast nutrients and an oxygen-bearing gas, the process comprising the steps of continuously withdrawing from the fermenting mixture a yeast- and alcohol-bearing wort which forms therein and separating from the withdrawn wort an alcohol-bearing medium, while continuously feeding to the mixture fresh aqueous slurry, the starter yeast, the yeast nutrients and the oxygen-bearing gas, the improvement wherein the yeast is a flocculating, bottom yeast, the portion of the wort which remains after separation of the alcohol-bearing medium therefrom, is recycled to the fermenting mixture, the oxygen-bearing gas is dispersed homogeneously throughout the fermenting mixture, and is introduced to maintain a mean-free oxygen concentration not greater than 1 ppm in the aqueous phase, and the process is controlled to maintain the measurable free sugar concentration in the fermenting mixture at a level which does not exceed 0.1 percent by weight, and to maintain the active yeast concentration in the fermenting mixture between 100 and 110 percent of the specific degree of fermentation.

2. In the process according to claim 1, the improvement wherein the oxygen-bearing gas is air.

3. In the process according to claim 1, the improvement wherein the residence period of the wort in the separation step is not greater than thirty minutes prior to separation of the alcohol-bearing medium therefrom.

4. In the process according to any of claims 1 to 3, the improvement wherein the alcohol-bearing medium separated from the wort is subjected to additional processing steps to obtain ethyl alcohol.

* * * * *